United States Patent [19]

Syriér

[11] 4,169,105
[45] Sep. 25, 1979

[54] PREPARATION OF CYANOACETATES

[75] Inventor: Johannes L. M. Syriér, Amsterdam, Netherlands

[73] Assignee: Shell Oil Company, Houston, Tex.

[21] Appl. No.: 941,341

[22] Filed: Sep. 11, 1978

[30] Foreign Application Priority Data

Sep. 19, 1977 [GB] United Kingdom ............... 38900/77

[51] Int. Cl.$^2$ ........................................... C07C 120/00
[52] U.S. Cl. .................... 260/465.4; 260/464; 260/465 D
[58] Field of Search ............................. 260/465.4, 464

[56] References Cited

U.S. PATENT DOCUMENTS

| 2,985,682 | 5/1961 | Raffelson | 260/465.4 X |
| 3,360,540 | 12/1967 | Sennewald et al. | 260/465.4 X |

FOREIGN PATENT DOCUMENTS

| 1210789 | 2/1966 | Fed. Rep. of Germany | 260/465.4 |
| 407890 | 4/1974 | U.S.S.R. | 260/465.4 |

OTHER PUBLICATIONS

Mills et al., Chem. and Ind., (1962), p. 2144.
Merker et al., J. Org. Chem., 26 (1961), pp. 5180–5182.

*Primary Examiner*—Joseph P. Brust

[57] ABSTRACT

Cyanoacetates of the formula

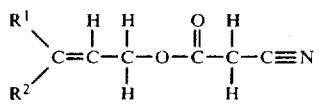

wherein $R^1$ and $R^2$ each independently is alkyl or cycloalkyl are prepared from cyanoacetic acid and the corresponding allylic halide in the presence of a hydrogen-halide acceptor and an inert organic solvent.

12 Claims, No Drawings

PREPARATION OF CYANOACETATES

BACKGROUND OF THE INVENTION

1. Field of the Invention

The present invention relates to a new process for the preparation of certain cyanoacetates.

2. Description of the Prior Art

R. L. Merker and M. J. Scott, J. Org. Chem., 26, pages 5108-2 (1961) describe the reaction of allyl chloride, triethylamine and acetic acid in acetone with a yield of only 35.8% of the allyl acetate.

By contrast the present invention provides for the preparation of certain cyanoacetate esters in very high yield and selectively (which is even as high as 100%) from a specific group of allylic halides and cyanoacetic acid.

SUMMARY OF THE INVENTION

The present invention is directed to a process for the preparation of a cyanoacetate of formula I

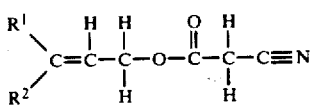

wherein $R^1$ and $R^2$ each individually represents an alkyl group or a cycloalkyl group, which process comprises treating cyanoacetic acid with an allylic halide of formula II

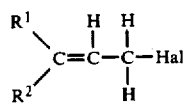

wherein $R^1$ and $R^2$ have the same meaning as defined above and Hal represents a halogen atom having an atomic number of at least 17, in the presence of a hydrogen-halide acceptor and an organic solvent which is substantially inert.

The selectivity to the compounds of formula I expressed in a percentage, is defined as a/b × 100 wherein "a" is the molar amount of the compound of formula II converted into the compound of formula I and "b" is the molar amount of converted compound of formula II.

$R^1$ and $R^2$ in formulas I and II preferably each individually represents a linear or branched alkyl group containing from 1 to 10 carbon atoms. More preferably, each of the symbols $R^1$ and $R^2$ represents a methyl group. Chlorine and bromine atoms are preferred among the halogen atoms that Hal in formula II may represent. The preferred starting compound of the general formula II is 1-chloro-3-methyl-2-butene. Other examples of compounds of formula II are 1-chloro-3-methyl-2-pentene, 1-chloro-3-ethyl-2-pentene, 1-chloro-3-ethyl-2-hexene and 1-chloro-3-cyclohexyl-2-butene and the compounds obtained by replacing the chlorine atom in each of these four compounds by a bromine atom.

The compounds of formula I are formed in notably high yield when the solvent is a halogenated hydrocarbon which is substantially inert, particularly a substantially inert chlorinated hydrocarbon having one to four carbon atoms per molecule, for example carbon tetrachloride, chloroform and perchloroethylene, or an aromatic hydrocarbon, particularly an alkylbenzene containing one or two alkyl groups of from 1 to 4 carbon atoms, for example toluene or a xylene or a mixture of xylenes. Carbon tetrachloride and toluene have proved very useful in this respect. Acetone is not a substantially inert solvent because compounds of formula

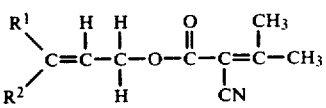

wherein $R^1$ and $R^2$ have the same meaning as defined hereinbefore, and water, are formed.

The process according to the present invention is carried out in the presence of a hydrogen-halide acceptor. The term hydrogen-halide acceptor is used to denote a compound that, when reacted with a hydrogen halide, forms an ammonium halide whether directly or indirectly, via a sequence of reactions. Examples of hydrogen-halide acceptors are primary, secondary and, particularly, tertiary amines. Among the tertiary amines trialkylamines are preferred. Very good results have been obtained with triethylamine. Other examples of tertiary amines are tri-n-propylamine, tri-n-butylamine, ethylmethyl-n-propylamine, tertbutyl-dimethylamine, dimethyloctadecylamine and pyridine. Another example of a hydrogen-halide acceptor is ammonia.

The molar ratios of cyanoacetic acid to the halide of the formula II and of cyanoacetic acid to the hydrogen-halide acceptor are not critical and may vary within wide limits. The former molar ratio is preferably in the range of from about 1:0.75 to about 1:1 and particularly of from about 1:0.95 to about 1:1. The latter molar ratio is preferably in the range of from about 1.25:1 to about 1:1 and particularly of from about 1.05:1 to about 1:1.

The process according to the present invention can be carried out in a wide temperature range. Temperatures in the range of from about 0° C. to 120° C., preferably from about 20° C. to about 100° C. are very suitable. The process is suitably carried out by stirring a mixture of the starting compounds, the hydrogen-halide acceptor and the substantially inert organic solvent for periods of up to five hours.

The ester of the formula I may be isolated from the reaction mixture by extracting the mixture with water, drying the raffinate phase obtained and distilling the dried liquid.

The cyanoacetate products of the present process are valuable chemical intermediates. 3-Methyl-2-butenyl cyanoacetate is a particularly useful pyrethroid acid intermediate. An enolate salt of this cyanoacetate is thermally rearranged as described in Belgian patent 847,534 to form a salt from which 2-cyano-3,3-dimethyl-4-pentenoic acid is liberated by acidification. This acid is reacted with carbon tetrachloride as described in Belgian Pat. No. 856,490 to form 4,6,6,6-tetrachloro-2-cyano-3,3-dimethylhexanoic acid. The latter acid is cyclized and dehydrochlorinated, followed by thermal decarboxylation of the resulting cyclized and dehydrohalogenated compound as described in Belgian Pat. No. 855,691 to form 2-(2,2-dichlorovinyl)-3,3-dimethylcyclopropanecarbonitrile. This carbonitrile is converted as described in Belgian Pat. No. 855,691 or in co-pending U.S. Ser. No. 923,133 into ethyl 2-(2,2-dichlorovinyl)-3,3-dimethylcyclopropanecarbonyl chloride. This carbonyl chloride is reacted with 3-phenoxybenzaldehyde and sodium cyanide with the formation of alpha-cyano-3-phenoxybenzyl 2-(2,2-dichlorovinyl)-3-dimethylcyclopropanecarboxylate as described in Belgian Pat. No. 851,900. This latter compound is a valuable pesticide of the pyrethrin type disclosed in U.S. Pat. No. 4,024,163. Such so-called "synthetic pyrethroids" combine exceptionally good insecticidal and/or acaricidal properties with a very low mammalian toxicity. This combination of properties makes them of considerable interest to the agrochemical industry and much effort has been expended to finding economic routes for the production of these "synthetic pyrethroids", particularly for the manufacture of substituted cyclopropanecarboxylic acids, which constitute the portion of the pyrethroid compounds for which no economical synthetic routes have been published so far in the literature.

ILLUSTRATIVE EMBODIMENTS

Embodiments I–IV-Preparation of 3-methyl-2-butenyl cyanoacetate

Cyanoacetic acid (25.9 mmol), 3-methyl-2-butenyl chloride (24.9 mmol), triethylamine (25.7 mmol) and a solvent (30 ml) were placed in a 50-ml flask equipped with a magnetic stirrer and a reflux condenser. The mixture was heated until no more of the title ester was formed. The Table states the solvents, temperatures and heating times used and presents the results. In all cases, the conversion of the 3-methyl-2-butenyl chloride was higher than 85%.

Table

| Embodiment | Solvent | Temp., °C. | Heating Time Hr. | Selectivity to The Title Ester % |
|---|---|---|---|---|
| I | carbon tetrachlorine | reflux | 3 | 100 |
| II | toluene | 80 | 4 | 97 |
| III | n-heptane | 80 | 5 | 98 |
| IV | cyclohexane | reflux | 7 | 98 |

Embodiment V-Preparation of 3-methyl-2-butenyl cyanoacetate

Cyanoacetic acid (259 mmol), 3-methyl-2-butenyl chloride (249 mmol), triethylamine (257 mmol) and toluene (200 ml) were placed in a 500-ml flask equipped with a paddle stirrer and a reflux condenser. The mixture was heated for 4 hours at 80° C. Then, the mixture was allowed to adopt a temperature of 20° C. and shaken with water (200 ml). The two phases formed were allowed to separate. The organic phase was isolated and dried over anhydrous magnesium sulphate. The dried liquid was distilled at a pressure of 4–5 mm Hg, leaving the title ester as a residue (boiling at 108°–110° C.) in a yield of 84%, calculated on starting 3-methyl-2-butenyl chloride.

I claim:

1. A process for the preparation of a cyanoacetate of the formula I $$\begin{array}{c} R^1 \\ \phantom{R^1}\diagdown \\ \phantom{R^1\diagdown}C{=}C{-}C{-}O{-}C{-}C{\equiv}N \\ \phantom{R^1\diagup}\diagup \\ R^2 \end{array} \quad (I)$$

wherein the $R^1$ and $R^2$ each individually represents an alkyl group or a cycloalkyl group, which process comprises treating cyanoacetic acid with an allylic halide of formula II $$\begin{array}{c} R^1 \\ \phantom{R^1}\diagdown \\ \phantom{R^1\diagdown}C{=}C{-}C{-}Hal \\ \phantom{R^1\diagup}\diagup \\ R^2 \end{array} \quad (II)$$

wherein $R^1$ and $R^2$ have the same meanings as defined above and Hal represents a halogen atom having an atomic number of at least 17, in the presence of a hydrogen-halide acceptor selected from tertiary amines or ammonia and an organic solvent which is substantially inert at a temperature in the range of from 0° C. to 120° C.

2. A process according to claim 1 wherein the substantially inert organic solvent is a halogenated hydrocarbon or aromatic hydrocarbon.

3. A process according to claim 2 wherein the halogenated hydrocarbon solvent is carbon tetrachloride, chloroform or perchloroethylene.

4. A process according to claim 3 wherein the aromatic hydrocarbon solvent is toluene, xylene or a mixture of xylenes.

5. A process according to claim 1 wherein the amine is a tertiary amine.

6. A process according to claim 5 wherein the tertiary amine is triethylamine, tri-n-propylamine, tri-n-butylamine, ethylmethyl-n-propylamine, tert-butyl-dimethylamine, dimethyloctadecylamine or pyridine.

7. A process according to claim 6 wherein the amine is triethylamine.

8. A process according to claim 2 wherein the molar ratio of cyanoacetic acid to the halide of formula II is in the range of 1:0.75 to 1:1.

9. A process according to claim 2 wherein the molar ratio of cyanoacetic acid to the hydrogen halide acceptor is in the range of 1.25:1 to 1:1.

10. A process according to claim 2 wherein $R^1$ and $R^2$ each individually represents an alkyl group containing from 1 to 10 carbon atoms.

11. A process according to claim 10 wherein $R^1$ and $R^2$ each represents a methyl group.

12. A process according to claim 10 wherein Hal in formula II is a chlorine or a bromine atom.

* * * * *